US011134850B2

United States Patent
Gaibazzi et al.

(10) Patent No.: US 11,134,850 B2
(45) Date of Patent: Oct. 5, 2021

(54) METHOD AND SYSTEM FOR MONITORING CARDIAC ARREST DURING A PHYSICAL EXERCISE OF A USER AND CONSEQUENT ACTIVATION OF A RESCUE REQUEST

(71) Applicant: HEART SENTINEL S.R.L., Parma (IT)

(72) Inventors: Nicola Gaibazzi, Parma (IT); Claudio Reverberi, Parma (IT)

(73) Assignee: HEART SENTINEL S.R.L., Parma (IT)

( * ) Notice: Subject to any disclaimer, the term of this patent is extended or adjusted under 35 U.S.C. 154(b) by 8 days.

(21) Appl. No.: 16/090,445

(22) PCT Filed: Jul. 26, 2016

(86) PCT No.: PCT/IB2016/054444
§ 371 (c)(1),
(2) Date: Oct. 1, 2018

(87) PCT Pub. No.: WO2017/168222
PCT Pub. Date: Oct. 5, 2017

(65) Prior Publication Data
US 2019/0200877 A1  Jul. 4, 2019

(30) Foreign Application Priority Data

Apr. 1, 2016 (IT) .................. 102016000033756

(51) Int. Cl.
*A61B 5/0205* (2006.01)
*A61B 5/00* (2006.01)
(Continued)

(52) U.S. Cl.
CPC ............ *A61B 5/0205* (2013.01); *A61B 5/002* (2013.01); *A61B 5/024* (2013.01); *A61B 5/1118* (2013.01);
(Continued)

(58) Field of Classification Search
CPC ....... A61B 5/0205; A61B 5/002; A61B 5/024; A61B 5/1118; A61B 5/6823;
(Continued)

(56) References Cited

U.S. PATENT DOCUMENTS 4,925,443 A * 5/1990 Heilman ................ A61N 1/365
600/16
5,718,235 A 2/1998 Golosarsky et al.
(Continued)

FOREIGN PATENT DOCUMENTS

GB    2 489 299 A    9/2012

OTHER PUBLICATIONS

International Search Report and Written Opinion of the International Searching Authority for International Patent Application No. PCT/IB2016/054444, dated Apr. 13, 2017, 15 pages.
(Continued)

*Primary Examiner* — Paula J Stice
(74) *Attorney, Agent, or Firm* — Merchant & Gould P.C.

(57) ABSTRACT

A method monitors cardiac arrest during physical exercise and consequently activates a rescue request. The method continuously measures a user's heart rate to determine a heart rate in a sequence of predetermined time intervals, by a heart rate measurement device worn by the user; then, generating a signal representative of the heart rate detected in each interval. A motion sensor detects a user's motion condition and generates a motion signal representative of the motion detected. A portable processor receives the heart rate signal and communicates with the heart rate measurement device and with the motion sensor; then processes the signal representative of heart rate, to recognize a possible cardiac arrest condition. The processor processes the motion signal to detect a possible stillness condition. The processor activates a rescue request if both a cardiac arrest condition and
(Continued)

a stillness condition have been recognized. A system executes the method.

15 Claims, 1 Drawing Sheet

(51) Int. Cl.
| | |
|---|---|
| *A61B 5/024* | (2006.01) |
| *A61B 5/11* | (2006.01) |
| *G08B 21/04* | (2006.01) |
| *G08B 25/00* | (2006.01) |
| *G08B 25/01* | (2006.01) |
| *G08B 25/08* | (2006.01) |
| *G08B 29/18* | (2006.01) |
| *A63B 24/00* | (2006.01) |
| *G08B 25/10* | (2006.01) |

(52) U.S. Cl.
CPC .......... *A61B 5/6823* (2013.01); *A61B 5/6831* (2013.01); *A61B 5/6898* (2013.01); *A61B 5/7282* (2013.01); *A61B 5/742* (2013.01); *A61B 5/7405* (2013.01); *A61B 5/747* (2013.01); *A61B 5/7465* (2013.01); *A61B 5/7475* (2013.01); *A63B 24/0062* (2013.01); *G08B 21/043* (2013.01); *G08B 21/0415* (2013.01); *G08B 21/0423* (2013.01); *G08B 21/0453* (2013.01); *G08B 21/0461* (2013.01); *G08B 21/0492* (2013.01); *G08B 25/001* (2013.01); *G08B 25/009* (2013.01); *G08B 25/016* (2013.01); *G08B 25/08* (2013.01); *G08B 25/10* (2013.01); *G08B 29/188* (2013.01); *A61B 5/02438* (2013.01); *A61B 5/1123* (2013.01); *A61B 2562/0219* (2013.01); *A63B 2024/0068* (2013.01); *A63B 2220/30* (2013.01); *A63B 2220/40* (2013.01); *A63B 2220/803* (2013.01); *A63B 2220/836* (2013.01); *A63B 2225/52* (2013.01)

(58) Field of Classification Search
CPC ... A61B 5/6831; A61B 5/6898; A61B 5/7292; A61B 5/7405; A61B 5/742; A61B 5/7465; A61B 5/02438; G08B 21/0453
See application file for complete search history.

(56) References Cited

U.S. PATENT DOCUMENTS

| | | | |
|---|---|---|---|
| 7,181,281 B1* | 2/2007 | Kroll | A61N 1/3622 607/14 |
| 2010/0298656 A1* | 11/2010 | McCombie | A61B 5/1114 600/301 |
| 2011/0298613 A1 | 12/2011 | Ben Ayed | |
| 2014/0288435 A1* | 9/2014 | Richards | A61B 5/14539 600/479 |
| 2015/0161876 A1* | 6/2015 | Castillo | G08B 21/0446 340/539.11 |
| 2016/0071392 A1 | 3/2016 | Hankey et al. | |
| 2016/0296170 A1* | 10/2016 | Putila | A61B 5/02444 |

OTHER PUBLICATIONS

Dekker, J.M. et al., "Low Heart Rate Variability in a 2-Minute Rhythm Strip Predicts Risk of Coronary Heart Disease and Mortality from Several Causes: The ARIC Study", Circulation, 102(11): 1239-1244 (2000).

* cited by examiner

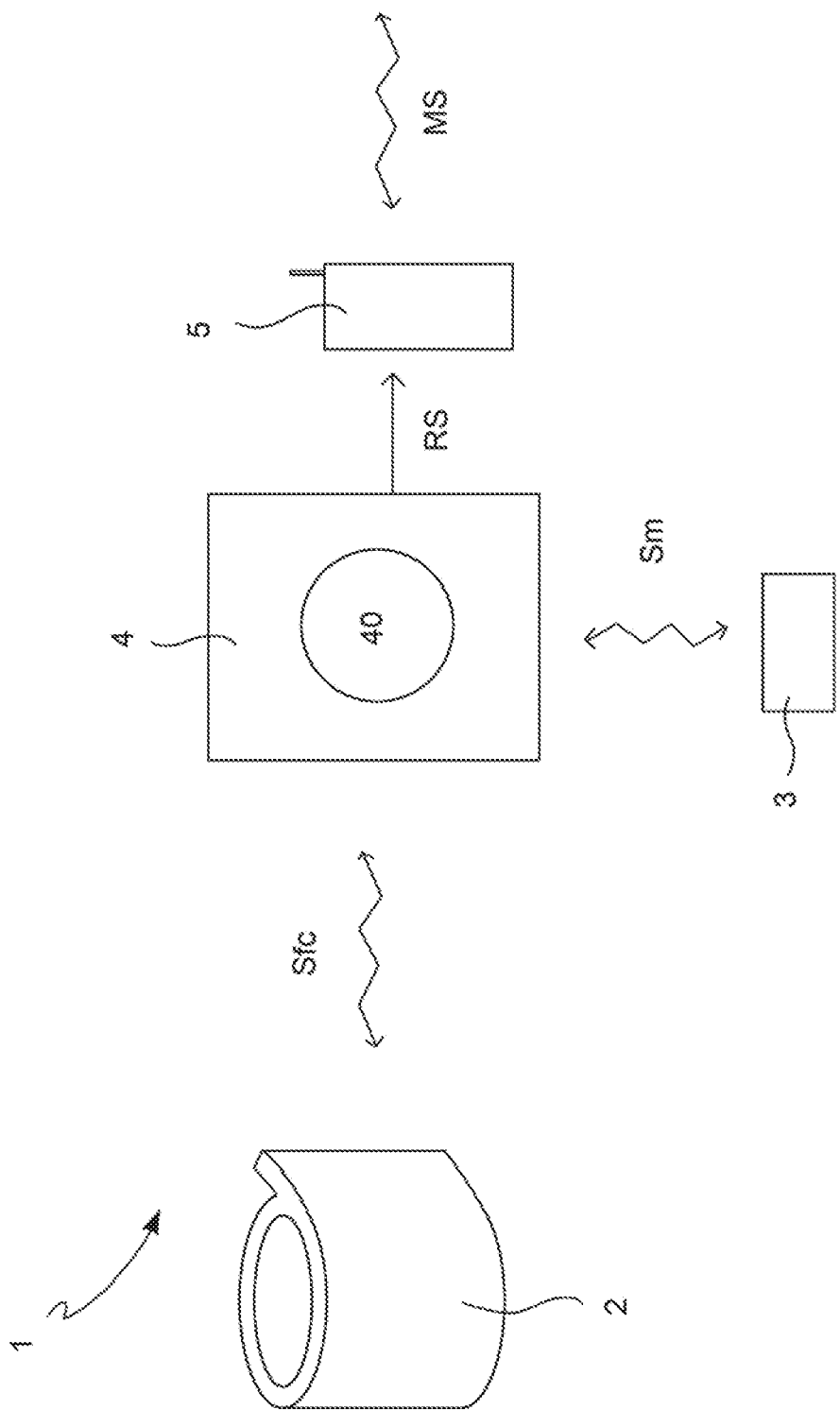

METHOD AND SYSTEM FOR MONITORING CARDIAC ARREST DURING A PHYSICAL EXERCISE OF A USER AND CONSEQUENT ACTIVATION OF A RESCUE REQUEST

This application is a National Stage Application of PCT/IB2016/054444, filed 26 Jul. 2016, which claims the benefit of Ser. No. 10/201,6000033756, filed 1 Apr. 2016 in Italy, and which applications are incorporated herein by reference. To the extent appropriate, a claim of priority is made to each of the above-disclosed applications.

TECHNOLOGICAL BACKGROUND OF THE INVENTION

Scope of Application

The present invention generally relates to the technical field of electronic systems for monitoring the health of a user during the execution of a physical exercise.

In particular, the invention relates to a method and a system for monitoring possible cardiac arrest during a user's physical exercise and consequently activating a rescue request.

Description of the Prior Art

It is known, in the medical-cardiological field, that the risk of cardiac arrest is higher during or just after strenuous physical exercise than in rest conditions.

It is also well known that cardiac arrest, for example associated with ventricular fibrillation or ventricular tachycardia, may have fatal consequences if nothing is done in an absolutely timely manner, for example by carrying out a defibrillation or another appropriate medical intervention; in particular, it is estimated that every minute that passes from the moment of cardiac arrest, the chances of survival are reduced by 10% and they substantially vanish after about ten minutes, in the absence of an appropriate intervention.

Therefore, if the cardiac arrest occurs in a place where no one can notice promptly, the chances for survival are substantially zero.

This situation can happen much more often than one believes, such as in cases of runners or joggers or cyclists or hikers who practice their physical activity outdoors, in a park or in the countryside or on the mountains, sometimes crossing not very popular places.

The importance of having methodologies and systems adapted to recognize the possible occurrence of cardiac arrest in a user performing physical activity and, when appropriate, to activate an alarm and/or an automatic rescue request is therefore apparent.

Of course, for reasons of cost, overall dimensions and convenience of use, it is quite impossible in this context to use sophisticated medical equipment for monitoring the cardiac cycle, such as those available in the hospital.

The need is therefore felt to have monitoring systems and methods that have limited costs and limited overall dimensions and can in practice be carried by a user (athlete, jogger, cyclist or other) during his/her physical exercise.

In this regard, heart rate monitoring systems have recently emerged which are based on automatic wrist measurement devices interoperating with applications available on smartphones or other mobile device, theoretically able to detect, for example, the absence of wrist pulse and therefore potentially able to automatically send alarm messages in such cases.

However, this solution has the drawback of sending false alarms with a relatively high probability, which is not acceptable for practical use.

In fact, the absence of wrist pulse may result from causes other than cardiac arrest (such as an incorrect position of the wrist detector, which can for example move frequently during running or exercise, or an even temporary malfunction of the wrist detector).

Even resorting to band monitoring devices (worn on the chest or other body part) able to detect the electrical activity of the heart, and therefore the heart rate, would not solve the problem of the reliability of recognizing a cardiac arrest condition. In fact, such band monitoring devices do not per se allow reliable diagnosis and detection of cardiac arrest, and also have a high and undesirable occurrence of "false alarms" or "false positives".

In summary, the prior art, on the one hand, proposes solutions that are reliable (in-hospital medical cardiac monitoring apparatuses) but not portable and therefore not usable during normal physical activity, or, on the other hand, solutions that are theoretically easy to use (e.g., wrist detector or chest band) but are not able to ensure sufficient reliability and overly likely to set off false alarms that nullify the purpose thereof.

In light of the above, a need is strongly felt for methods and systems for monitoring cardiac arrest during physical exercise and for activating a rescue request which are realistically usable in the context in question and which at the same time reduce (ideally to zero) the possibility of "false alarms".

SUMMARY OF THE INVENTION

The object of the present invention is to provide a method for monitoring cardiac arrest during physical exercise and activating a rescue request which allows at least partially overcoming the drawbacks mentioned above with reference to the prior art and meeting the above needs particularly felt in the relevant technical field.

Another object of the present invention is a system for monitoring cardiac arrest during physical exercise and for activating a rescue request.

BRIEF DESCRIPTION OF THE DRAWINGS

Further features and advantages of such a system and method according to the invention will become apparent from the following description of preferred embodiment examples, made by way of a non-limiting example with reference to the accompanying FIGURE, in which:

FIG. 1 shows a simplified block diagram of a monitoring system according to an embodiment of the present invention.

DETAILED DESCRIPTION

With reference to FIG. 1, a method is now described for monitoring cardiac arrest during physical exercise and consequently activating a rescue request. The method comprises the steps of continuously measuring a user's heart rate to determine a heart rate in each of a sequence of time intervals having predetermined duration, by means of a heart rate measurement device 2 worn by the user; then, again by means of the heart rate measurement device 2, generating a signal representative of the heart rate Sfc measured in each of the time intervals.

The method further provides continuously detecting a user's motion condition and generating a motion signal Sm representative of the motion detected, by means of at least one motion sensor 3 with which the user is provided.

The method then comprises the steps of receiving said signal representative of the heart rate Sfc and said motion signal Sm by means of a user portable processor device 4, communicating with the heart rate measurement device 2 and with the at least one motion sensor 3.

The method then comprises the steps, by means of the portable processor device 4, of processing the signal representative of the heart rate Sfc to recognize a possible cardiac arrest condition based on a real-time analysis of the continuously measured heart rate; and processing the motion signal Sm to detect a possible stillness condition of the user.

The method finally includes activating a rescue request RS by the portable processing device 4 if, in the processing steps, a cardiac arrest condition and, at the same time, a stillness condition of the user have been recognized.

It is noted that, as described above, the method contemplates monitoring the user's heart rate, not the wrist pulse. In fact, the method aims to recognize various situations of serious cardiac arrhythmias subtending cardiac arrest, in which, as is known in the medical field, the heart rate is not zero but on the contrary becomes higher than normal and/or very irregular, corresponding to a condition of ventricular fibrillation and/or ventricular tachycardia.

It is also noted that the activation of the rescue condition is only carried out in the presence of both the monitored alarm conditions, namely the abnormal heart rate and the simultaneous stillness of the user. In this way, advantageously, it is possible to prevent or substantially reduce the likelihood of sending false alarms.

According to an embodiment of the method, the step of processing the signal representative of the heart rate Sfc includes continuously measuring the heart rate difference measured in consecutive time intervals; comparing said difference with one or more variation thresholds that are predetermined as acceptable (for example, suitable to define normal values associated with the physical exercise considered); recognizing a condition of cardiac arrest when the heart rate difference exceeds said one or more variation thresholds for a predetermined number of times over the duration of a predetermined first number of consecutive time intervals.

It is noted that in this embodiment, an abnormal heart rate irregularity is evaluated, which is another indicative, very significant signal of the occurrence of arrhythmias such as a ventricular fibrillation which causes cardiac arrest.

According to an implementation example of the above embodiment, the frequency detection time interval is 1 second; heart rate difference variation thresholds in consecutive time intervals are +7 and −7; the predetermined number of times the threshold must be exceeded to generate the alarm is greater than or equal to 2; the duration within which such a number of anomalies must possibly be found is 40 consecutive intervals (defined above as "the first number of consecutive time intervals").

According to other implementation examples of said embodiment, said parameters (frequency detection time interval, difference variation thresholds, predetermined number of times the threshold is exceeded and first number of consecutive time intervals) can take values other than those given above as an example, but in any case pre-configured.

According to another embodiment of the method, the step of processing the signal representative of the heart rate includes recognizing a cardiac arrest condition when the heart rate measured remains constant at a fixed value along the duration of a predetermined second number of consecutive time intervals.

According to an implementation option, such a second number of consecutive time intervals is 20. In fact, a duration of 20 seconds in which a heart rate is constant at a fixed value, without any variation, indicates a non-physiological and unrealistic condition, therefore being potentially pathological and index of possible cardiac arrest.

According to other implementation options, such a second number of consecutive time intervals is different than 20, as long as it meets the criterion above, according to which the corresponding duration indicates a non-physiological condition.

According to another embodiment of the method, the step of processing the signal representative of the heart rate includes the steps of comparing the heat rate detected in each time interval with a predetermined frequency threshold and recognizing a cardiac arrest condition when the heart rate detected is higher than said frequency threshold for a predetermined third number of consecutive time intervals.

According to an implementation example of said embodiment, the frequency detection time interval can be 1 second; the number of consecutive time intervals in which the anomaly is recorded (defined above as "third number of consecutive time intervals") can be 25; the threshold frequency can for example be 170 pulses per minute. It is noted that this value is not always and necessarily related to a condition of cardiac arrest; however, due to the correlation with the motion detection, which is described in more detail hereinafter, such a threshold value can be considered effective.

According to other implementation examples of said embodiment, said parameters (detection time interval, frequency thresholds, third number of consecutive time intervals) can take values other than those given above as an example, but in any case pre-configured.

According to further embodiments of the method, multiple procedures of recognition of cardiac arrest, among those described above, can be provided in combination with each other.

In such cases, the step of recognizing cardiac arrest includes recognizing a condition of cardiac arrest when a heart rate difference exceeds one or more variation thresholds for a predetermined number of times over the duration of a predetermined first number of consecutive time intervals; and/or when the heart rate measured remains constant at a fixed value over the duration of a predetermined second number of consecutive time intervals; and/or when the heart rate detected exceeds a frequency threshold for a predetermined third number of consecutive time intervals.

In such cases, therefore, as symptoms of anomalies, one or more conditions are detected and the probable occurrence of cardiac arrest is recognized on the basis of all the information gathered at the occurrence of one, several or all the predetermined anomaly conditions.

According to an embodiment of the method, said receiving and processing steps are carried out by a software program or application 40 stored in and executable by the portable processor device 4.

According to an implementation option, said heart rate measurement device 2 is a cardiac monitoring band wearable on the chest or on another part of the user's body. For example, a sports performance monitoring chest band may be used, per se known and/or available on the market, able to measure the heart rate based on a detection of the electrical activity of the heart.

Advantageously, the decision criteria, parameters and recognition thresholds mentioned above can be set flexibly, by means of the software application, taking into account also the type of monitoring band that is actually used.

According to an implementation option of the method, said at least one motion sensor 3 is an accelerometer or a speed sensor or a gyroscope or a compass. Such a sensor may for example be worn or carried in any way by the user, or built in a device carried by the user.

According to an implementation option of the method, the signal representative of the heart rate Sfc and the motion signal Sm are electric signals adapted to be wirelessly transmitted; in this case, the communication between the heart rate measurement device 2 and the portable processor device 4 is a wireless communication.

For example, such a wireless communication is a BLUETOOTH™ wireless data transfer communication, taking advantage of such well-known and widespread short-range wireless communication technology.

According to an embodiment of the method, the step of activating a rescue request RS comprises sending a rescue request message MS by means of a user mobile communication device 5 interoperating with the portable processor device 4, upon receiving the rescue request RS generated by the portable processor device 4.

According to an implementation example of the method, the portable processor device 4, the motion sensor 3 and the mobile communication device 5 are implemented and integrated into a smartphone.

In that case, the processing software program 40, mentioned above, may be made available in the form of application ("app") for a smartphone.

According to a further embodiment, the method comprises the further step of providing the user, before activating the rescue request, with a visual and/or audible message to allow disabling the rescue request procedure so that the user, if healthy and conscious, can disable the rescue request procedure.

In that case, the method provides for proceeding with the step of activating the rescue request if, after a predetermined period of time, the user does not answer to the message to allow disabling the rescue request procedure.

According to an embodiment embodiment, the method includes the further step of determining the user's location using a geolocation system built in the processing device 4 or in the mobile communication device 5 of the user.

In that case, the step of activating the rescue request procedure includes sending information about the user's location.

A system 1 for monitoring a cardiac arrest during a user's physical exercise and consequently activating a rescue request is now described. The system comprises a heart rate measurement device 2 wearable by the user, at least one user-portable motion sensor 3, and a user-portable processor device 4.

The heart rate measurement device 2 which can be worn by the user is configured to continuously measure the user's heart rate, determine a heart rate in each of a sequence of time intervals of predetermined duration, and generate a signal representative of the heart rate Sfc determined in each of the time intervals.

The at least one motion sensor 3 which can be carried by the user is configured to detect a motion condition of the user and generate a motion signal Sm representative of the motion detected.

The portable processor device 4 is adapted to communicate with the heart rate measurement device 2 and with the at least one motion sensor 3.

The portable processor device 4 is configured to receive and process the signal representative of the heart rate Sfc and the motion signal Sm. Processing the signal representative of the heart rate Sfc allows recognizing, during monitoring, a possible condition of cardiac arrest on the basis of the heart rate measured; processing the motion signal Sm allows recognizing, during monitoring, a possible stillness of the user.

The portable processor device 4 is further configured to activate a rescue request, if a cardiac arrest condition and, at the same time, a stillness condition of the user have been recognized.

According to an embodiment, the system comprises a software program or application 40, stored in and executable by the portable processor device 4, wherein the software program or application 40 are able to perform the above steps of receiving, processing, and activating.

According to an implementation option of the system, the heart rate measurement device 2 includes a cardiac monitoring band wearable on the chest or on another part of the user's body. For example, a sports performance monitoring chest band may be used, per se known and/or available on the market, able to measure the heart rate based on a detection of the electrical activity of the heart.

According to different implementation options of the system, said at least one motion sensor 3 is an accelerometer or a speed sensor or a gyroscope or a compass.

According to an embodiment of the system, both the heart rate measurement device 2 and the portable processor device 4 comprise a wireless transceiver, and the communication between the heart rate measurement device 2 and the portable processor device 4 is a wireless communication.

According to an implementation example, said wireless transceivers are short-range wireless transceivers, such as BLUETOOTH™ wireless data transfer transceivers.

According to an embodiment, the system further comprises a user mobile communication device 5 interoperating with the portable processing device 4.

According to an embodiment of system 1, the portable processor device, the motion sensor 3 and the mobile communication device 5 are implemented and integrated into a smartphone.

According to several possible implementation examples, system 1 is configured to execute a method according to any one of the above embodiments.

As can be seen, the object of the present invention is fully achieved by the method and by the system described above, by virtue of their functional and structural features.

Firstly, the above illustrated method is based on the monitoring of the heart rate and not of the user's wrist pulse. This allows recognizing various situations of cardiac arrest with greater reliability, for example most conditions of cardiac arrest in which, as is known in the medical field, the heart rate is not zero but becomes higher than normal and/or very irregular, corresponding to a condition of ventricular fibrillation and/or ventricular tachycardia.

Secondly, the processing of the signals received, described above, allows further improving the reliability of recognition of a cardiac arrest (although the level of accuracy of medical equipment for hospital use cannot be achieved).

Moreover, the activation of the rescue request is only carried out in the presence of both the monitored alarm conditions, namely the abnormal heart rate and the simultaneous stillness of the user.

In this way, advantageously, it is possible to prevent or substantially reduce the likelihood of sending false alarms. In fact, if detection of the cardiac arrest is a false alarm, therefore detected while the user is continuing his/her exercise, the motion sensor would indicate a motion condition (or in any case, not a condition of absolute stillness), which would allow blocking and not sending a rescue request recognized as unjustified.

This feature allows also obviating the non-absolute accuracy that intrinsically emerges in the case of monitoring carried out only on the heart rate, rather than on the entire electrocardiographic graph, and by means of a "sports" commercial device rather than by a medical apparatus (impractical in this application scope).

Similar advantages can be identified with reference to the system, described above, able to execute the method of the invention.

A person skilled in the art may make several changes, adjustments, adaptations and replacements of elements with other functionally equivalent ones to the embodiments of the system and method according to the invention in order to meet incidental needs, without departing from the scope of the following claims. Each of the features described as belonging to a possible embodiment can be obtained independently of the other embodiments described.

The invention claimed is:

1. A method for monitoring cardiac arrest during physical exercise and consequently activating a rescue request, comprising the steps of:
   continuously measuring a heart rate of a user to determine a heart rate in each of a sequence of time intervals having predetermined duration, by a heart rate measurement device worn by the user;
   generating a signal representative of the heart rate measured in each of the time intervals, by the heart rate measurement device;
   continuously detecting a motion condition of the user and generating a motion signal representative of motion detected, by at least one motion sensor with which the user is provided;
   receiving said signal representative of the heart rate and said motion signal by a user portable processor device, communicating with the heart rate measurement device and with the at least one motion sensor;
   processing the signal representative of heart rate, by the portable processor device, to recognize a possible cardiac arrest condition based on a real time analysis of the heart rate measured;
   processing the motion signal by the portable processor device to detect a possible stillness condition of the user;
   wherein if, in said processing steps, a cardiac arrest condition and, at a same time, a stillness condition of the user have been recognized, activating a rescue request by the portable processing device;
   wherein the step of processing the signal representative of the heart rate comprises:
   continuously measuring a difference between the heart rates measured in consecutive time intervals;
   comparing said difference with one or more predetermined variation thresholds, defining normal difference values associated with the physical exercise;
   recognizing the cardiac arrest condition when the heart rate difference exceeds said one or more variation thresholds for a predetermined number of times along a duration of a predetermined first number of consecutive time intervals.

2. The method according to claim 1, wherein the step of processing the signal representative of the heart rate comprises:
   recognizing the cardiac arrest condition when the heart rate measured remains constant at a fixed value along a duration of a predetermined second number of consecutive time intervals.

3. The method according to claim 1, wherein the step of processing the signal representative of the heart rate comprises:
   comparing the heart rate measured at each time interval with a predetermined rate threshold;
   recognizing a cardiac arrest condition when the heart rate measured is higher than said rate threshold for a predetermined third number of consecutive time intervals.

4. The method according to claim 1, wherein said receiving and processing steps are carried out by a software program or application stored in and executable by the portable processor device.

5. The method according to claim 1, wherein said signal representative of the heart rate and motion signal are electric signals adapted to be wirelessly transmitted, and wherein the communication between the heart rate measurement device and the portable processor device is a wireless communication.

6. The method according to claim 1, wherein the step of activating rescue request comprises sending a rescue request message by a user mobile communication device interoperating with the portable processor device, upon receiving the rescue request generated by the portable processor device.

7. The method according to claim 1, comprising providing the user, before activating the rescue request, with a visual and/or audible message to allow disabling the rescue request procedure so that the user, if healthy and conscious, can disable the rescue request procedure; and
   wherein the method provides for proceeding with the step of activating the rescue request if, after a predetermined period of time, the user does not answer to the message to allow disabling the rescue request procedure.

8. A system for monitoring a cardiac arrest during a user's physical exercise and consequently activating a rescue request, comprising:
   a heart rate measurement device adapted to be worn by a user, configured to continuously measure the user's heart rate, determine a heart rate in each of a sequence of time intervals of predetermined duration, and generate a signal representative of the heart rate determined in each of the time intervals;
   at least one motion sensor adapted to be carried by the user, configured to detect a motion condition of the user and generate a motion signal representative of the motion detected;
   a user portable processor device adapted to communicate with the heart rate measurement device and with the at least one motion sensor;
   the portable processor device being configured to:
   receive said signal representative of the heart rate and said motion signal;
   continuously process the signal representative of the heart rate to recognize a possible cardiac arrest condition based on the heart rate determined, wherein to continuously process the signal representative of the heart rate, the portable processor device is configured to:

continuously measure a difference between the heart rates measured in consecutive time intervals, compare said difference with one or more predetermined variation thresholds, defining normal difference values associated with the physical exercise, recognize the cardiac arrest condition when the heart rate difference exceeds said one or more variation thresholds for a predetermined number of times along the duration of a predetermined first number of consecutive time intervals;

continuously process the motion signal for detecting a possible stillness condition of the user;

activate a rescue request, if a cardiac arrest condition and, at the same time, a stillness condition of the user have been recognized.

9. The system according to claim 8, comprising a software program or application, stored in and executable by the portable processor device, the software program or application being adapted to perform the steps of receiving, processing, and activating.

10. The system according to claim 8, wherein said heart rate measurement device comprises a cardiac monitoring band wearable on a chest or on another part of the user's body.

11. The system according to claim 8, wherein said at least one motion sensor is an accelerometer or a speed sensor or a gyroscope.

12. The system according to claim 8, wherein both the heart rate measurement device and the portable processor device comprise a wireless transceiver; and wherein the communication between the heart rate measurement device and the portable processor device is a wireless communication.

13. The system according to claim 12, wherein said wireless transceiver is a Bluetooth transceiver.

14. The system according to claim 8, further comprising a user mobile communication device interoperating with the portable processing device.

15. The system according to claim 14, wherein the portable processor device, the motion sensor and the mobile communication device are implemented and integrated into a smartphone.

* * * * *